United States Patent
Seipler et al.

(10) Patent No.: US 6,650,121 B2
(45) Date of Patent: Nov. 18, 2003

(54) SENSOR FOR THE MONITORING OF AN $NO_X$ CATALYST

(75) Inventors: Dieter Seipler, Reutlinger (DE); Bernd Schumann, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/236,848

(22) Filed: Sep. 6, 2002

(65) Prior Publication Data

US 2003/0011374 A1 Jan. 16, 2003

Related U.S. Application Data

(63) Continuation of application No. 09/254,603, filed as application No. PCT/DE97/01714 on Aug. 12, 1997.

(30) Foreign Application Priority Data

Sep. 5, 1996 (DE) .......................................... 196 35 977

(51) Int. Cl.[7] ............................................. G01N 27/407
(52) U.S. Cl. ........................ 324/446; 324/439; 204/421; 204/446
(58) Field of Search ............................ 324/446, 207.13, 324/230, 219, 529, 663, 439; 204/421, 408, 425, 426

(56) References Cited

U.S. PATENT DOCUMENTS

| 4,303,613 A | 12/1981 | Yasuda et al. ................. 422/95 |
| --- | --- | --- |
| 4,692,429 A | 9/1987 | Sekido et al. ................ 502/303 |
| 5,015,616 A | 5/1991 | Sekido et al. ................ 502/303 |
| 5,369,956 A | 12/1994 | Daudel et al. ................. 60/276 |
| 5,444,974 A | 8/1995 | Beck et al. .................... 60/274 |
| 5,546,004 A | 8/1996 | Schmelz ..................... 324/446 |

FOREIGN PATENT DOCUMENTS

EP 0 560 991 9/1993

*Primary Examiner*—Jay Patidar
*Assistant Examiner*—Vincent Q. Nguyen
(74) *Attorney, Agent, or Firm*—Kenyon & Kenyon

(57) ABSTRACT

A sensor for the monitoring of an $NO_x$ catalyst having a storage material for the adsorption of $NO_x$, the storage material forming the sensitive element of the sensor. As a result, it is possible to measure the instantaneous degree of charging of the storage material, and a quasi-linear control for the storage of $NO_x$ is made possible. The ability to precisely monitor the degree of charging of the storage material makes it possible to better utilize the storage capacity, and the catalyst can be dimensioned in a more cost-effective manner. The conversion phase of the rich side can be predicted more precisely and consequently be integrated more favorably into the driving cycle. The sensor for the monitoring of an $NO_x$ catalyst is especially suitable for installation in the exhaust path of an internal combustion engine with direct gasoline injection or of a diesel engine.

19 Claims, 1 Drawing Sheet

SENSOR FOR THE MONITORING OF AN $NO_x$ CATALYST

CROSS-REFERENCE TO RELATED APPLICATIONS

This application is a continuation of prior application Ser. No. 09/254,603, filed Jun. 9, 1999, which is the U.S. national phase of PCT/DE97/01714, filed Aug. 12, 1997.

BACKGROUND INFORMATION

The conventional three-way catalyst for the cleaning of the exhaust gas of internal combustion engines removes the exhaust components HC, CO and $NO_x$ in a very efficient manner, however, only under the predominant condition in the driving cycle that the exhaust gas composition approximates the stoichiometric air-fuel ratio. For oxidizing exhausts, such as in lean mix engines and diesel engines, the $NO_x$ adsorption/reduction catalyst has gained wide acceptance, the catalyst operating according to the following principle: during the predominant phase of lean exhaust output in the driving cycle, $NO_x$ is accumulated in the adsorber material to be then desorbed and reduced in a rich pulse. Such an $NO_x$ catalyst is described in European Patent Application No. 0 560 991. Alkali metals, alkaline earth metals, rare earth metals and noble metals are named therein as adsorber substances which are applied to a carrier material such as aluminum oxide. The adsorption of oxygen in the form of $O_2^-$ in the lean phase is named as an assumed reaction mechanism, the $O_2^-$ reacting with the $NO_x$ from the exhaust to form $NO_2$. A portion of the $NO_2$ formed is further oxidized and diffused in the adsorber material in the form of nitrate ions. In the event of a shift of the exhaust composition to rich, the above-named reaction sequence takes place in the opposite direction, i.e., $NO_x$ is reduced to free nitrogen with the reducing components HC and CO of the richer exhaust. The catalyst operates predominantly in the lean phase; the time ratio of the lean phase to the rich pulse is approximately 50:1.

A significant problem is the ability to identify when the storage capacity of the adsorber material is exhausted and the rich pulse must be initiated. For this purpose according to European Patent Application No. 0 560 991, the cumulative speed of the vehicle is measured and the degree of charging of the adsorber material is estimated from it. Exact knowledge of the degree of charging is not possible with this method.

SUMMARY OF THE INVENTION

The sensor according to the present invention has the advantage that the instantaneous degree of charging of the storage material of the catalyst is measured and a quasi-linear control for the storage of $NO_x$ is made possible.

The ability to precisely monitor the degree of charging of the storage material makes it possible to better utilize the storage capacity, and the catalyst can be dimensioned in a more cost-effective manner. The conversion phase of the rich side can be predicted more precisely and consequently be integrated more favorably into the driving cycle.

Having the storage material of the catalyst serve at the same time as the base element for the sensor for charge measurement results in a space saving and cost saving method in relation to a sensor located downstream of the catalyst.

In a favorable manner, the sensor is constructed in such a way that it responds to an electrical or electromagnetic characteristic of the storage material which changes with the adsorbed quantity of $NO_x$. In a particularly simple manner, the sensor can be designed as a capacitor, the capacitance of which changes with the dielectric constant, which in turn is a function of the degree of charging of the storage material.

In an advantageous manner, the sensor may also be designed as a resonator, a cavity resonator or a filled waveguide; in contrast to a planar capacitor, this makes more voluminous structures possible which are capable of containing a greater quantity of $NO_x$. In addition, the influence of the storage material on the electrical or electromagnetic value to be measured is intensified, since it is possible to measure at a higher frequency.

A capacitor is preferably suitable for lower frequencies; if the plate dimensions approach the order of magnitude of the wavelength of the electromagnetic waves, the signals can no longer be interpreted easily.

DETAILED DESCRIPTION

Figure 1:
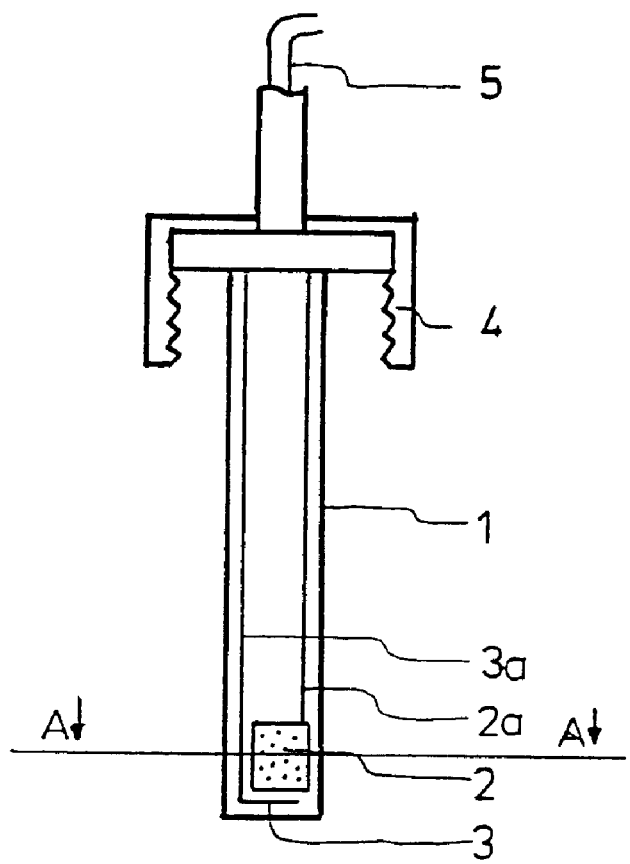
FIG. 1 shows a simplified representation of a sensor according to the present invention.
Figure 2:
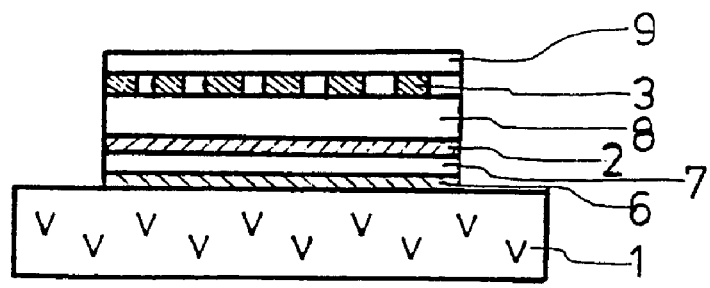
FIG. 2 shows a cross-section through the electrode area of the sensor along line A—A of FIG. 1.

In FIGS. 1 and 2, a sensor is shown as an exemplary embodiment in the form of a planar sensor similar to the well-known lambda sensor used for the measurement of the air-fuel ratio. The sensor is installed in an $NO_x$ storage catalyst which is not shown.

A heater 6 with a cover 7, a bottom electrode 2 with a supply lead 2a, a layer 8 containing the storage material of the $NO_x$ catalyst and a cover electrode 3 with a supply lead 3a are applied in vertically arranged layers to a planar ceramic carrier 1 which is preferably made of aluminum oxide. A sensor without heater can, however, also be used.

Customary electrode materials such as platinum or platinum group metals are used for the electrodes. The cover electrode is made up of porous grains which are conductively bonded to each other and make the access of the exhaust gas to storage material 8 possible.

Used as the storage material are customary $NO_x$ storage materials such as alkali metals, alkaline earth metals, rare earth metals and/or noble metals which are applied to a carrier.

The sensor may carry a porous cover 9 as a mechanical protective layer and/or as a catalytic layer.

The electrical connections for the electrodes and heater are guided via a supply lead 5. The sensor is attached in the $NO_x$ catalyst, which is not shown, via cap nut 4.

The change of an electrical or electromagnetic characteristic of the catalyst-storage material is used as the sensor principle.

If the sensor according to the present invention is placed in an $NO_x$—containing gas stream, for example, in the exhaust stream of a lean mix engine or a diesel engine, the storage material of the catalyst is increasingly charged with $NO_x$.

At the same time, as the concentration of polar $NO_x$ molecules increases, the dielectric constant of the storage material changes and consequently the capacitance of a capacitor, for example, the dielectric material of which is the storage material. It is possible in this manner to measure the instantaneous degree of charging of the storage material. If the storage capacity of the catalyst is exhausted, a rich pulse is generated via a suitable device and the $NO_x$ desorption is thus brought about in the known manner.

The sensor according to the present invention can be brought to a suitable temperature range in which no accumulation of water or other components takes place via a heater 6, resulting in an improvement of cross-sensitivity.

The suitable selection of a covering layer makes it possible to catalyze any preliminary reactions that may be required and to ensure mechanical protection.

According to the present invention, however, other characteristics of the catalyst-storage material which change with the adsorbed $NO_x$ quantity may also serve as the basis for the sensor; these include dielectric losses, permeability, magnetic losses or resistance per unit length. These parameters can be measured particularly well in a resonator, cavity resonator or a filled waveguide. Moreover, the catalyst itself can be inserted completely or partially or as a separator in one of the above-named sensor structures in a form identical to the original catalyst or modified from it. The named sensors are based on a common principle, the attenuation of an electromagnetic field by condensation of the polar $NO_x$ molecules on the storage material.

The charging state can also be determined by measurement of the adsorption of electromagnetic radiation by the molecules of the adsorbed gas, the combinations of this gas with the storage material, in particular.

What is claimed is:

1. A planar sensor for monitoring an $NO_x$ catalyst, comprising:
   a planar ceramic carrier;
   a heater layer;
   a cover layer for the heater layer;
   a bottom electrode layer having a first supply lead;
   a storage material layer containing a $NO_x$ storage material;
   a cover electrode layer having a second supply lead; and
   a supply lead coupled to the first supply lead and the second supply lead;
   wherein:
      the heater layer; the bottom electrode layer, the storage material layer and the cover electrode layer are applied in vertically arranged layers to the planar ceramic carrier; and
      changes in at least one of an electrical and an electromagnetic characteristic of the storage material layer correspond to the amount of $NO_x$ in the storage material layer.

2. The planner sensor of claim 1, wherein:
   the heater layer is arranged on the planar ceramic carrier;
   the cover layer is arranged between the heater layer and the bottom electrode; and
   the storage material layer is arranged between the cover layer and the electrode layer.

3. The planner sensor of claim 1, wherein the planar ceramic carrier is made of aluminum oxide.

4. The planar sensor of claim 1, wherein each of the electrode layers is made from a platinum group metal.

5. The planner sensor of claim 1, wherein the cover electrode layer is made of porous grains that are conductively bonded to each other so that an exhaust gas may access the storage material layer.

6. The planner of claim 1, further comprising a porous cover layer arranged on the cover electrode layer.

7. The planner sensor of claim 6, wherein the porous cover layer functions as at least one of a mechanically protective layer and a catalytic layer.

8. The planner sensor of claim 1, wherein the at least one of the electrical and electromagnetic characteristics includes a permeability of the storage material layer.

9. The planner sensor of claim 1, wherein the at least one of the electrical and electromagnetic characteristics include a permeability of the storage material layer.

10. The planner sensor of claim 1, wherein the at least one of the electrical and electromagnetic characteristics includes a resistance per unit length of the storage material layer.

11. A planner sensor for monitoring an $NO_x$ catalyst, comprising:
   a planar ceramic carrier;
   a heater layer;
   a cover layer for the heater layer;
   a bottom electrode layer having a first supply lead;
   a storage material layer containing a $NO_x$ storage material; and
   a cover electrode layer having a second supply lead;
   a supply lead coupled to the first supply lead and the second supply lead;
   wherein:
      the heater layer; the bottom electrode layer, the storage material layer and the cover electrode layer are applied in vertical arranged layers to the planar ceramic carrier;
      changes in at least one of an electrical and an electromagnetic characteristic of the storage material layer correspond to the amount of $NO_x$ in the storage material layer;
      the heater layer is arranged on the planar ceramic carrier;
      the cover layer is arranged between the heater layer and the bottom electrode;
      the storage material layer is arranged between the cover layer and the cover electrode layer; and
      the cover electrode layer is made of porous grains that are conductively bonded to each other so that an exhaust gas may access the storage material layer.

12. The planar sensor of claim 11, further comprising a porous cover layer arranged on the cover electrode layer.

13. The planar sensor of claim 11, wherein the planar ceramic carrier is made of aluminum oxide.

14. The planar sensor of claim 11, wherein each of the electrode layers is made from a platinum group metal.

15. The planar sensor of claim 11, further comprising a porous cover layer arranged on the cover electrode layer.

16. The planar sensor of claim 15, wherein the porous cover layer functions as at least one of a mechanically protective layer and a catalytic layer.

17. The planar sensor of claim 11, wherein the at least one of the electrical and electromagnetic characteristics includes a dielectric constant of the storage material layer.

18. The planar sensor of claim 11, wherein the at least one of the electrical and electromagnetic characteristics includes a permeability of the storage material layer.

19. The planar sensor of claim 11, wherein the at least one of the electrical and electromagnetic characteristics includes a resistance per unit length of the storage material layer.

* * * * *

UNITED STATES PATENT AND TRADEMARK OFFICE
CERTIFICATE OF CORRECTION

PATENT NO.    : 6,650,121 B2
DATED         : November 18, 2003
INVENTOR(S)   : Dieter Seipler et al.

It is certified that error appears in the above-identified patent and that said Letters Patent is hereby corrected as shown below:

Column 3,
Lines 52, 58 and 62, change "The planner sensor" to -- The planar sensor --
Line 66, change "The planner of claim 1," to -- the planar sensor of claim 1 --

Column 4,
Lines 1, 4, 7 and 10, change "The planner sensor" to -- The planar sensor --
Line 13, change "A planner sensor" to -- A planar sensor --
Line 28, change "the heater layer;" to -- the heater layer, --

Signed and Sealed this

Twenty-fifth Day of January, 2005

JON W. DUDAS
*Director of the United States Patent and Trademark Office*